United States Patent [19]

Goble et al.

[11] Patent Number: 4,997,433
[45] Date of Patent: Mar. 5, 1991

[54] ENDOSTEAL FIXATION STUD AND SYSTEM

[76] Inventors: E. Marlowe Goble, 850 E. 1200 North; W. Karl Somers, 651 N. 150 West, both of Logan, Utah 84321

[21] Appl. No.: 465,914

[22] Filed: Jan. 16, 1990

[51] Int. Cl.$^5$ .............................................. A61F 2/08
[52] U.S. Cl. ...................................... 606/64; 606/62; 623/13; 623/16
[58] Field of Search ...................... 606/62, 63, 64, 65, 606/68, 53; 623/13, 16, 16 A; 411/509, 510; 439/324, 818, 846, 848

[56] References Cited

U.S. PATENT DOCUMENTS

| | | | |
|---|---|---|---|
| 3,744,488 | 7/1973 | Cox | 606/64 |
| 4,301,551 | 11/1981 | Dore et al. | 623/13 |
| 4,388,921 | 6/1983 | Sutter et al. | 623/16 X |
| 4,688,561 | 8/1987 | Reese | 606/64 |
| 4,772,286 | 9/1988 | Goble et al. | 623/13 |

Primary Examiner—Robert A. Hafer
Assistant Examiner—Kerry Owens
Attorney, Agent, or Firm—M. Reid Russell

[57] ABSTRACT

An endosteal fixation for mounting a prosthetic or soft tissue graft or combination thereof, under tension at a cortex end of a bone tunnel and process for its use. The endosteal fixation stud includes a cylindrical body that is preferably manufactured from a somewhat resilient material, and is suitable for implantation in a human body. The cylindrical body is stepped outwardly, proximate to a rear end, into a bridge that has spaced rearwardly extending arms wherebetween the graft is secured. The cylindrical body forward end is split into equal parallel sections that can be flexed together, one of which sections includes a hook that extends and rearwardly, that will align with the cylindrical body surface when the two cylindrical body sections are compressed together. The endosteal fixation stud can be arranged to be pushed or pulled through a bone tunnel. A single endosteal fixation stud is utilized to mount a graft and to the cortex at a bone tunnel end, the graft extending therefrom through the tunnel and out the opposite bone tunnel end, whereat it is bent and secured under tension, as with a staple, to the cortex surface adjacent to that bone tunnel end.

26 Claims, 2 Drawing Sheets

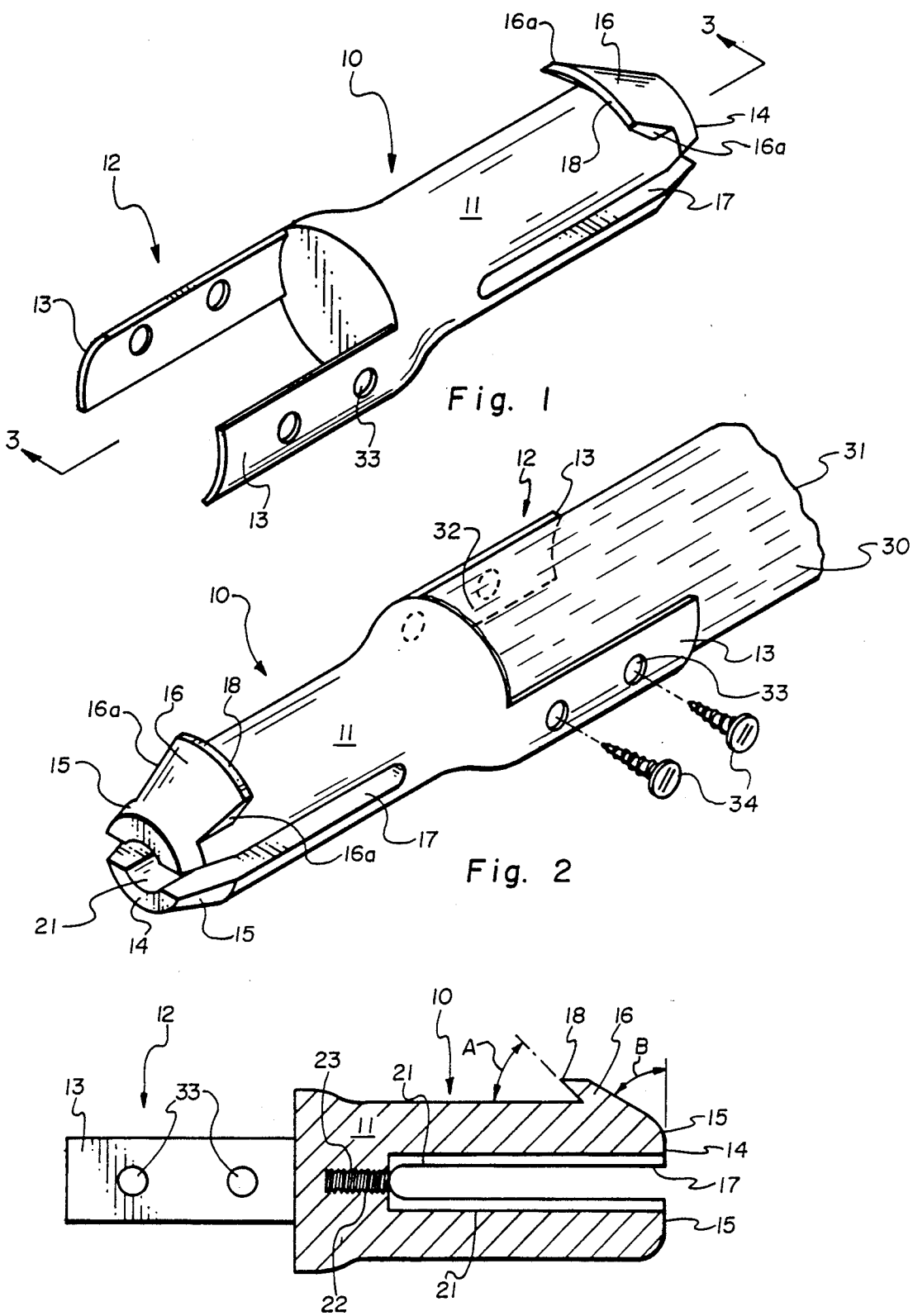

ENDOSTEAL FIXATION STUD AND SYSTEM

BACKGROUND OF THE INVENTION

1. Field of the Invention

This invention relates to ligament anchor systems and devices for use in arthroscopic surgical procedures involving securing an end of a ligament, such as the anterior cruciate ligament, stint, or the like, under tension within a bone mass.

2. Prior Art

In certain ligament replacement surgical procedures, particularly arthroscopic knee surgery, involving a cruciate ligament replacement, it is usual to form a tunnel through bone masses on both sides of a joint for installing a ligament therein. Such installation has generally involved fitting the ligament through the prepared tunnel and attaching its ends onto the bone cortex surfaces as with staples, or the like, for maintaining the ligament under tension across the joint. Examples of arrangements for attaching ligament ends within a bone mass are shown in a United Kingdom patent, No. G.B. 2,084,468A; and a patent of the present inventors, U.S. Pat. No. 4,772,286. A U.S. patent application of the present inventors, application Ser. No. 235,194, entitled "Channel Ligament Clamp and System", shows a device for securing a ligament end onto a bone mass. Additionally, another earlier patent of the present inventors, U.S. Pat. No. 4,870,957, entitled "Ligament Anchor System", shows a stud for mounting a ligament end within a ligament tunnel that involves a threaded sleeve or footing that is turned into a tapped endosteal bone. Another U.S. patent application of the present inventors, application Ser. No. 352,153, entitled "Interference Screw, System and Process", provides an interference screw and system for turning it into a ligament tunnel, alongside a ligament end therein.

All of the above-cited devices and systems involve hardware and systems for connection of a ligament to the endosteal portion of the distal femur, and the "Ligament Anchor System" application involves a separate stud and footing for mounting a ligament end to bone. Whereas, the present invention employs a single stud only that is for insertion to closely fit in a ligament tunnel and to lock into the cortex surface, and is arranged for mounting a ligament end to a rear end thereof. The stud of the present invention is for sliding along the prepared ligament tunnel. The stud forward end sections are split by a slot, allowing the section to be squeezed together as the stud is urged into the tunnel. The stud forward end, as it emerges from a cortex end of the ligament tunnel, flexes outwardly, a hook end section of the stud to extend beyond the tunnel edge. Which hook edge thereby binds into the surrounding bone mass or over the outer cortex when the stud is pulled back into the ligament tunnel, securely and permanently mounting that stud end to that bone cortex.

SUMMARY OF THE INVENTION

It is a principal object of the present invention to provide an endosteal fixation system for mounting a ligament in a bone tunnel.

Another object of the present invention is to provide an endosteal fixation stud that is for closely fitting through a straight bone tunnel that is formed at an angle to the bone cortex surface, the stud to include a hook end that exits the tunnel cortex end and flexes outwardly thereat, the hook end edge to flex over the tunnel cortex edge, locking thereto and prohibiting withdrawal of that stud back through the bone tunnel.

Another object of the present invention is to provide an endosteal fixation stud with an arrangement for mounting it to a ligament end, the stud and ligament for fitting in a prepared ligament bone tunnel, the stud to travel therealong, a stud hook end on exiting which tunnel to flex over the bone cortex tunnel edge, prohibiting withdrawal of that stud and ligament back through the tunnel.

Still another object of the present invention is to provide an endosteal fixation stud that is formed from a suitable material for human implantation that will exhibit resilient qualities.

Still another object of the present invention is to provide an endosteal fixation stud whereto can be attached a ligament or the like, which stud is for locking into the end of a bone tunnel formed through the femur and is preferably re-absorbable.

The present invention is in an endosteal fixation stud and system for permanently mounting a ligament end, or the like, within a bone tunnel. The stud is a cylindrical section having a slightly smaller diameter than does a bone tunnel wherein a ligament end is to be mounted. Which bone tunnel is formed at an angle to the plane of the bone cortex tunnel end whereby a hook end of the stud will flex over, as to lock onto the edge of that bone cortex surface. Which angle is optimally forty-five (45) degrees but may be in a range of angles between twenty-five (25) degrees and sixty-five (65) degrees, within the scope of this disclosure.

The endosteal fixation stud consists of a cylindrical body that preferably includes a bridge arrangement at its rear most end for attaching a ligament graft, or the like, mounted between parallel legs thereof. The nose of the stud cylindrical body is preferably flared outwardly and rearwardly at approximately a sixty (60) degree angle to the vertical forming an arcuate segment as a hook end. An outer edge of which hook end is to extend beyond the bone tunnel edge for binding into or onto the bone cortex. To allow the stud with outwardly extending hook end to slide along the ligament tunnel, a longitudinal slot is formed in that stud forward end to approximately a mid-point thereof. The slot divides the stud end into segments, that, when compressed as when the stud is fitted through the bone tunnel, will flex together, and will spring apart on exiting the tunnel end. To provide this flexure, the stud is preferably formed from a resilient material that is suitable for human implantation, such as a resilient metal or a plastic like DELRIN ™, polyethene or re-absorbable material.

Additionally, a bridge, or the like, that includes an arm or spaced arms is provided as a stud end for use in attaching a ligament end. Further, a threaded suture, wire or rod can be used with the invention for turning into a tapped hole that is formed in the stud forward end, the suture, wire or rod for pulling the stud through a bone tunnel. Whereafter, the suture, wire or rod is removed by turning it out of that stud end tapped end hole.

In practice, for securing an end of a ligament, or like graft, either biological or prosthetic, utilizing the endosteal fixation stud of the present invention, a tunnel is formed through a bone or bones, for receiving the ligament. The bone tunnel is to receive the stud and, provide a proper binding surface therefore. Accordingly, it is preferably angled from the plane of bone cortex surface at approximately a forty-five (45) degree angle, plus or minus twenty (20) degrees to conform to the angle of the stud hook end. So arranged, a ligament end is attached at the bridge rear end of the stud cylindrical body. The stud is to travel through the bone tunnel and exit the bone cortex surface. On exiting, the stud hook end will flex or spring outwardly, an edge thereof extending beyond to rest on the tunnel edge. With tension then applied through the ligament, that anchor stud hook edge will seat into the bone cortex, prohibiting ligament withdrawal back through the bone tunnel.

In one installation procedure of an anterior cruciate ligament, a first endosteal fixation stud mounting a anterior cruciate is urged through a bone tunnel, the stud hook edge emerging from a femoral cortex end to bind into the bone at the tunnel edge. This passage can involve passing the suture, wire or rod, threaded end first, through the femoral cortex tunnel end to the tibial cortex end. Thereat, the stud is turned onto that wire or rod end. The suture, rod or wire is then drawn back through the ligament tunnel, with the connected stud and ligament drawn therewith until the stud hook end extends beyond and is pulled back to engage the bone tunnel femoral cortex end. The ligament free end is then placed under tension at the tibial cortex end as by attaching it with a standard staple, or the like, to the cortex surface. Alternatively, the endosteal femoral fixation stud can be fitted through an arthroscopic port into the patient's knee and pushed with an appropriate instrument outwardly through the femoral bone tunnel section from within the intra articular joint, and with the free ligament end fitted from the intra articular joint through the tibial bone tunnel section.

To release a stud hook end, the stud forward end sections can be collapsed together, until the hook end edge aligns with the ligament tunnel wall. The stud can thereafter be pushed back into the ligament tunnel, allowing for its removal.

DESCRIPTION OF THE DRAWINGS

In the drawings that illustrate that which is presently regarded as the best mode for carrying out the invention:

FIG. 1 is a side elevation perspective view taken from a rear end of an endosteal fixation stud of the present invention;

FIG. 2 is a side elevation perspective view of the endosteal fixation stud of FIG. 1 taken from a forward end and showing a ligament mounted between opposing parallel flanges of a stud rear end;

FIG. 3 is a side elevation sectional view taken along the line 3—3 of FIG. 1;

DETAILED DESCRIPTION

Figure 4:
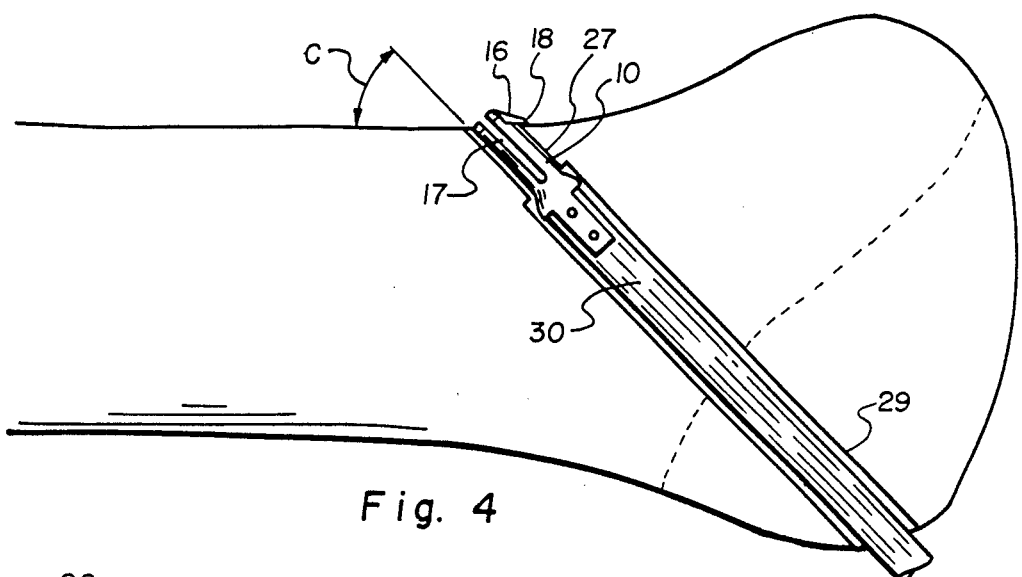
FIG. 4 is a side elevation view of a longitudinal cross-section of a distal femur wherein a ligament tunnel has been formed, and counter-sunk to accommodate a endosteal fixation stud of the present invention fitted therein that includes a ligament mounted thereto.

FIG. 1 shows a side elevation perspective view taken from a rear end of the present invention in an endosteal fixation stud 10 of the present invention, hereinafter referred to as stud. Stud 10, as shown best in FIGS. 1 through 3, includes a cylindrical body 11 that includes body 12 as a rear end. The bridge 12 includes spaced apart parallel arms 13 that extend parallel to one another and rearwardly from the face of the cylindrical body. A stud forward or front end 14 is shown in FIGS. 2 and 3 as rounded at 15. Which stud front end includes an arcuate section that is formed into a hook 16, as shown in FIGS. 1, 2 and 3.

The hook 16 is formed as an outwardly and rearwardly projecting extension of a section of the stud cylindrical body front end 14, extending rearwardly from the rounded forward end 15. The hook 16, as shown best in FIG. 3, is preferably angled at approximately forty-five (45) degrees rearwardly from the cylindrical body 11 surface, which angle is illustrated as arrow A, and is preferably the angle of a bone tunnel to a bone cortex. A forward face of the hook 16 is shown formed at approximately a sixty (60) degree angle from the vertical plane of the stud front end 14, illustrated as arrow B. In practice, the hook is preferably formed as a section of less than one hundred eighty (180) degrees of arc, and has essentially parallel opposite edges 16a, with a hook edge or lip 18, and is an extension of the stud forward or front end.

As will be discussed in greater detail hereinbelow, the stud 10 is intended to fit into and travel along a bone tunnel that is formed through a bone mass, shown herein as the distal femur, exiting the anterolateral cortex. Which bone tunnel is counter-sunk to just accommodate the stud cylindrical body forward end at the anterolateral cortex exit, which anterolateral cortex end is of lesser cross-section than the cross-section of the stud forward end with the stud hook 16 extended. Accordingly, to allow for collapse of the stud hook 16, to where the stud will slide therethrough the femoral tunnel section, a slot 17, as shown in FIGS. 1 through 3, is formed longitudinally into the stud cylindrical body. This slot splits that cylindrical body to approximately the mid-point thereof. So arranged, the opposite slot edges are spaced apart equidistantly along the slot, the stud sections capable of being collapsed together.

The slot 17 is to allow the sections of the stud cylindrical body 11, at the hook end, to be squeezed together. The hook edge or lip 18 is thereby recessed to where it can be fitted into the ligament tunnel. At the anterolateral cortex end of which tunnel, the cylindrical body sections to flex or return to their uncompressed state, extending the hook edge 18 over the tunnel edge. That hook edge 18 will thereby bind into a section of the bone surrounding that tunnel end when the stud is pulled back into the bone tunnel. To provide which flexure the stud 10 is formed from a resilient material, such as DELRIN ™ plastic material, or the like, but can also be formed of an appropriate metal, as required.

Shown in FIG. 2, the bridge 12 is formed as the rear end of the cylindrical body and is stepped outwardly as the parallel spaced apart arms 13. Which arms 13 are to receive a ligament end 31 fitted therebetween. Shown best in FIG. 2, the ligament end 31 is preferably secured between the stud arms 13 as with screws 34, that are fitted through aligned holes 33 that are formed through the stud arms. Which screws preferably pass through both the ligament end 31 and a bone plug 32 that is arranged as a stiffener with that ligament end. The bone plug 32 is shown as provided to wedge the ligament end between which arms 13, as well as for receiving the screws 34 turned therein.

Alternative to bridge 12, the stud 10 rear end can be provided with a screw extending rearwardly therefrom, not shown, from turning into the ligament 30 end, or can involve an eyelet end, not shown, for receiving a ligament and/or stint, not shown, threaded therethrough.

Figure 5:
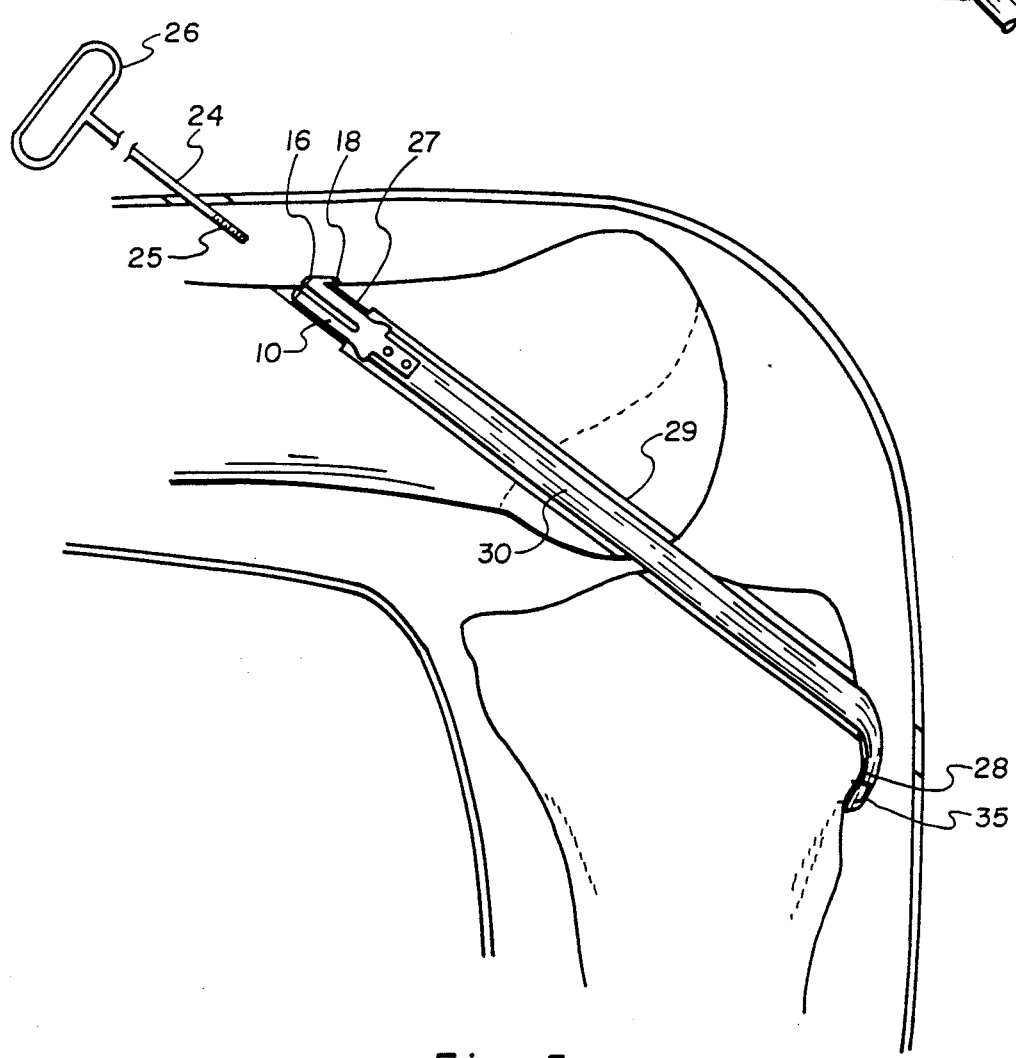
FIG. 5 is a side elevation sectional view of a patient's knee wherein a ligament tunnel has been formed in an anterior cruciate ligament replacement surgical procedure, showing the ligament of FIG. 4 connected at its one end to the endosteal fixation stud, with the ligament free end extending beyond and bent onto the tibial cortex whereat it is secured by a staple.

The stud forward end 14, as shown best in FIG. 2, preferably includes longitudinal parallel arcuate grooves 21 that are formed in the center of the slot 17 opposing surfaces. As shown best in FIG. 3, a center longitudinal hole 22 is formed into the end of stud slot 17 that is tapped with threads 23. Which hole 22 aligns with, as an end of, the arcuate grooves 21. The hole 22, as shown in broken lines in FIG. 5, is to receive a threaded end 25 of a suture, wire or rod. In FIG. 5, a wire or rod 24 is shown that preferably includes a handle 26 formed on the opposite end thereof to threaded end 25, which handle is for manually guiding and turning the wire or rod threaded end 25 into the threads 23 of the stud longitudinal hole 22. So connected, an operator can move the stud 10 as by pulling or pushing on handle 26 along the bone tunnel. In such travel, the stud cylindrical body sections are compressed into slot 17, the arcuate grooves 21 to collapse towards the wire or rod 24.

FIGS. 4 and 5 illustrate an example of a practice of a process of the present invention for replacing a patient's anterior cruciate ligament 30. Which procedure can be adapted to provide a bone/tendon/bone attachment, and the ligament 30 can be a prosthetic or soft tissue graft or a combination or composite thereof. The process utilizes a stud 10 with a ligament end 31 attached to the stud bridge 12. The ligament end is maintained rearwardly between arms 13 of bridge 12. That other end of which ligament, as shown in FIG. 5, extends from the tibial cortex end 28 of bone tunnel 29. The ligament 30, as shown in FIG. 5, is bent back onto the tibia cortex surface, and receives a staple 35 straddling that ligament for maintaining the ligament under tension to the bone surface. The stud 10 is for maintaining the ligament 30 stretched through the bone tunnel 30 to the bone at the femoral cortex tunnel end. The bone tunnel 29 is initially formed to have a diameter to just accommodate the stud 10. Thereafter, the bone tunnel is counterbored, as bone tunnel section 29, to have a diameter to freely accommodate the stud bridge 12 with ligament 30 attached thereto, a femoral tunnel end 27, shown in FIGS. 4 and 5 to just accommodate stud 10. The femoral tunnel end 27, for proper stud 10 functioning, should exit the femoral cortex at an angle that is the angle of the rear face of the stud hook 16 relative to the cylindrical body 11. Which angle is preferably forty-five (45) degrees plus or minus twenty (20) degrees, for proper stud hook 16 functioning.

In an arthroscopic surgical procedure, through an opening, not shown, that is formed into the patient's intra articular joint, a surgeon can manipulate stud 10 into the bone tunnel femoral end and can urge that stud, as with a tool, not shown, along the tunnel section until the hook 16 extends beyond the femoral cortex edge. Whereat the stud hook edge overlaps the tunnel edge securing the connected femoral end of ligament 30 in the femur section of the bone tunnel. Additionally, a stint, not shown, can be attached to extend from the stud bridge 12, within the scope of this disclosure.

In another installation procedure, as illustrated in FIG. 5, the wire or rod 24 threaded end 25 can be fitted through the femoral bone tunnel cortex end 27 and turned into the threads 23 of hole 22 formed in stud 10. So arranged, a surgeon gripping the wire or rod handle 26 can pull the stud 10 mounted thereto through the femoral end of the bone tunnel, the attached ligament following therethrough to where the hook 16 of the stud extends beyond the bone tunnel femoral cortex end. Thereat, the hook edge or lip 18 will engage and, with an application of a tensile force on the ligament 30 at its tibial end, will bind or bite into the cortex surface. The hook edge 18 thereby prohibits withdrawal of the stud 10 back through the bone tunnel. To secure the free ligament 10 tibial end, that end is pulled beyond the tibial cortex tunnel end and is bent onto the bone surface. A staple, or like fastener, like staple 35, is then driven into the tibial cortex, the staple web compressing the ligament against the bone surface.

The stud 10, along with a staple 35, or like fastener, provides a tension mounting of ligament 30, with or without a stint across the intra articular joint. Which tension can be readily adjusted by urging the stud 10 outwardly from the bone tunnel femoral cortex and freeing the hook edge 18 by compressing the stud sections across slot 17 together, the stud hook 16 thereby allowed to pass into the tunnel femoral cortex end. The stud can thereafter be pulled back through the bone tunnel 29, allowing for a ligament length adjustment to provide a desired tensile force on the ligament when the stud is reinstalled to the femoral cortex tunnel end, as set out above.

In practice, a stud 10 installed as set out above in a cadaver knee was found to provide a stable and secure ligament anchor up to an application of approximately two hundred (200) pounds of tensile force. Which force is well above an mean functional load for an anterior or posterior cruciate ligament of approximately one hundred (100) pounds of tensile force.

While a preferred embodiment of the present invention and process for securing a ligament in a ligament tunnel have been shown and described herein, it should be understood that the present disclosure is made by way of example only and that variations and changes thereto are possible without departing from the subject matter and reasonable equivalency thereof coming within the scope of the following claims, which claims we regard as our invention.

We claim:

1. An endosteal fixation stud comprising, a cylindrical body that has a diameter to closely fit in a cortex end of a bone tunnel that is formed appropriately in a bone mass, which cylindrical body from a forward end thereof is slotted longitudinally, splitting said forward end into two segments; and an arcuate hook means is secured to an end of one of said two segments extending outwardly and rearwardly therefrom, an outer edge of which said arcuate hook means is above the plane of said cylindrical body and can be flexed inwardly to below said plane when said two segments are flexed together.

2. An endosteal fixation stud as recited in claim 1, wherein the endosteal fixation stud is manufactured from a resilient material that is suitable for human implantation and will allow for flexure together of the two cylindrical body segments.

3. An endosteal fixation stud as recited in claim 2, wherein the endosteal fixation stud is manufactured from a plastic material that may be re-absorbable.

4. An endosteal fixation stud as recited in claim 1, wherein the cylindrical body forward end, at one of the two equal segments is sloped into a forward face of the arcuate hook means.

5. An endosteal fixation stud as recited in claim 4, wherein the arcuate hook means is less than one hundred eighty (180) degrees of arc across its forward face, and said forward face is formed at an angle of approximately sixty (60) degrees to a vertical plane at the cylindrical body forward end.

6. An endosteal fixation stud as recited in claim 4, wherein a rear face of the slope of the arcuate hook means to the surface of the cylindrical body is the same angle as the angle of the bone tunnel to the bone mass surface.

7. An endosteal fixation stud as recited in claim 6, wherein the arcuate hook rear face is angled at an angle of from twenty-five (25) to sixty-five (65) degrees to the cylindrical body surface.

8. An endosteal fixation stud as recited in claim 1, further including a bridge means that is secured to the cylindrical body rear end, which said bridge means includes spaced apart essentially parallel rearwardly facing arm means for receiving an end of a graft therebetween; and means for securing said graft end between said bridge means arm means.

9. An endosteal fixation stud as recited in claim 8, wherein the bridge means arm means are stepped outwardly from the cylindrical body surface; and the means for securing the graft end are screws fitted through each said arm means.

10. An endosteal fixation stud as recited in claim 8, further including a bone plug means that is arranged as a sandwich with the graft end, for facilitating mounting said graft end between the bridge means arms.

11. An endosteal fixation stud as recited in claim 1, further including means for moving the bone anchor stud through a bone tunnel.

12. An endosteal fixation stud as recited in claim 11, wherein the means for moving the endosteal fixation stud through the bone tunnel is a center tapped hole that is formed longitudinally into the end of the longitudinal slot; and a rod means having a threaded end for turning in said tapped hole.

13. An endosteal fixation stud as recited in claim 12, further including longitudinal groove means formed in the opposing surfaces of the cylindrical body segments for accommodating the rod means fitted therebetween; and said rod means end opposite to the threaded end includes a handle means for manual manipulation.

14. A process for mounting a natural, prosthetic or soft tissue graft in tension in a prepared bone tunnel consisting of the steps of, attaching an end of a graft to an endosteal fixation stud, which said endosteal fixation stud includes, with a cylindrical body, arrangements for directly securing a forward end thereof to a bone cortex and for mounting a graft to its opposite rear end; and forming a bone tunnel between femoral and tibial cortex surfaces, where, at least one said bone tunnel cortex end has a diameter to accommodate said endosteal fixation stud forward end fitted therein to connect to said bone cortex.

15. A process as recited in claim 14, wherein, the endosteal fixation stud includes, as the arrangement for directly securing a forward end thereof to a bone cortex, an outwardly extending hook formed on the forward end of the cylindrical body, which said cylindrical body is split longitudinally from said hook end forming opposing parallel sections that will flex together at said forward end such that an outer edge of said hook will align with said stud cylindrical body surface; and said outer edge of said hook will flex outwardly when emerging from said bone tunnel cortex end to engage and bind into said bone cortex.

16. A process as recited in claim 15, wherein the endosteal fixation stud includes, as the arrangement for mounting a graft to its end, a bridge that includes spaced apart parallel arms that are for receiving therebetween said graft; and installing connectors between said bridge arms, through said graft.

17. A process as recited in claim 16, wherein the bone tunnel is counter-bored to below the bone cortex end for accommodating travel of the endosteal fixation stud bridge and ligament therealong.

18. A process as recited in claim 15, wherein the bone tunnel is formed at an angle to the bone cortex surface to accommodate the endosteal fixation stud hook edge binding to said bone cortex surface.

19. A process as recited in claim 18, wherein the bone tunnel is formed at an angle of from twenty-five (25) to sixty-five (65) degrees to the femoral anterolateral cortex surface.

20. A process as recited in claim 15, wherein the graft end that is opposite to the endosteal fixation stud end is pulled from the opposite bone cortex tunnel end and is bent to engage that cortex surface; and a fastener is installed in that cortex surface for maintaining that graft end secured in tension on said cortex surface.

21. A process as recited in claim 14, further including, connecting the endosteal fixation stud releasably to a rod means to move that rod means through the bone tunnel to where that endosteal fixation stud engages and secures to the cortex of said bone tunnel end.

22. A process as recited in claim 14, further including, from within an intra articular joint wherethrough the bone tunnel is formed, fitting an endosteal fixation stud and connected prosthetic or soft tissue graft end arthroscopic port or opening into said intra articular joint, and urging that endosteal fixation stud into the bone tunnel to where that endosteal fixation stud will engage and mount to the bone tunnel cortex end.

23. A process as recited in claim 14, wherein a straight tunnel is formed when the femoral and tibial segments are aligned.

24. A process as recited in claim 14, wherein the endosteal fixation stud is a stud having a cylindrical body, a forward end of which is slotted longitudinally to a mid-point so as to provide sections that can be urged together, one of which said sections includes an outwardly projecting hook that has an edge that will pass over and lock into the femoral anterolateral cortex.

25. A process as recited in claim 24, wherein the graft is secured to extend from the endosteal fixation stud cylinder body end opposite to the forward slotted end; and the femoral and tibial tunnel segments are enlarged to accommodate travel of said graft and its coupling to said endosteal fixation stud.

26. A process as recited in claim 21, further including pulling the endosteal fixation stud, from the tibial end, through the aligned femoral and tibial segments to where said endosteal fixation stud engages and secures to the cortex of said femoral segment; and attaching, under tension, the graft end to the tibial cortex with a staple driven into said tibial cortex, the staple legs straddling said prosthetic or soft tissue graft end.

* * * * *